United States Patent
Lee et al.

(10) Patent No.: US 9,064,329 B2
(45) Date of Patent: Jun. 23, 2015

(54) METHOD OF RECONSTRUCTING IMAGE AND APPARATUS AND TOMOGRAPHY APPARATUS FOR PERFORMING THE SAME

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Jong-ha Lee, Hwaseong-si (KR); Young-hun Sung, Hwaseong-si (KR); Kang-eui Lee, Seoul (KR); Kwang-eun Jang, Busan (KR); Seung-ryong Cho, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 282 days.

(21) Appl. No.: 13/780,346

(22) Filed: Feb. 28, 2013

(65) Prior Publication Data

US 2013/0294568 A1 Nov. 7, 2013

(30) Foreign Application Priority Data

May 7, 2012 (KR) .................... 10-2012-0048313

(51) Int. Cl.
G06T 5/50 (2006.01)
A61B 6/00 (2006.01)
G06T 11/00 (2006.01)

(52) U.S. Cl.
CPC ...... *G06T 5/50* (2013.01); *A61B 6/52* (2013.01); *G06T 11/005* (2013.01); *G06T 2211/432* (2013.01)

(58) Field of Classification Search
CPC ...... G06T 5/50; G06T 2211/432; G06T 11/005; A61B 6/00
USPC ............................................ 378/4, 9; 382/131
See application file for complete search history.

(56) References Cited

U.S. PATENT DOCUMENTS

| 7,751,528 | B2 * | 7/2010 | Zhou et al. ................. 378/37 |
| 2011/0311020 | A1 * | 12/2011 | Lee et al. ................... 378/9 |
| 2012/0076260 | A1 * | 3/2012 | Kitagawa et al. .......... 378/41 |
| 2012/0300901 | A1 * | 11/2012 | Lewalter et al. .......... 378/22 |

FOREIGN PATENT DOCUMENTS

| JP | 2011-072346 A | 4/2011 |
| JP | 2011-083499 A | 4/2011 |
| KR | 10-2008-0010674 A | 1/2008 |
| KR | 10-2011-0045319 A | 5/2011 |

* cited by examiner

Primary Examiner — Irakli Kiknadze
(74) Attorney, Agent, or Firm — Sughrue Mion, PLLC (57) ABSTRACT

A method of reconstructing a tomography image of an object from a plurality of projection images generated by scanning the object in a plurality of projection directions includes: determining whether a truncated portion of the object exists in the plurality of projection images; reconstructing a first reconstruction image; calculating projection data for the first reconstruction image; and reconstructing a tomography image of the object by using the calculated projection data.

20 Claims, 7 Drawing Sheets

METHOD OF RECONSTRUCTING IMAGE AND APPARATUS AND TOMOGRAPHY APPARATUS FOR PERFORMING THE SAME

CROSS-REFERENCE TO RELATED APPLICATION

This application claims the priority from Korean Patent Application No. 10-2012-0048313, filed on May 7, 2012, in the Korean Intellectual Property Office, the disclosure of which is incorporated herein in its entirety by reference.

BACKGROUND

1. Field

Apparatuses and methods consistent with inventive concept relate to reconstructing an image in tomography apparatuses.

2. Description of the Related Art

A medical imaging system emits radiation, for example, X-rays, toward a subject such as a human body by using a radiation source, and generates an image of the subject by detecting radiation that has passed through the subject by using a detector. In this case, in order to reconstruct a tomography composition image of the subject, the radiation source may emit radiation toward the subject while moving linearly or in a circular arc around the subject.

SUMMARY

Exemplary embodiments may address at least the above problems and/or disadvantages and other disadvantages not described above. Also, exemplary embodiments are not required to overcome the disadvantages described above, and an exemplary embodiment may not overcome any of the problems described above.

One or more exemplary embodiments provide methods of reconstructing tomography images having improved accuracy.

One or more exemplary embodiments further provide apparatuses and tomography apparatuses for performing the methods.

One or more exemplary embodiments further provide non-transitory computer-readable recording media having recorded thereon a program for executing the methods.

According to an aspect of an exemplary embodiment, a method of reconstructing a tomography image of an object from a plurality of projection images generated by scanning the object in a plurality of projection directions includes: determining whether a truncated portion of the object exists in each of the plurality of projection images; reconstructing a first reconstruction image by using at least one projection image, in which a truncated portion of the object does not exist, based on a result of the determining; calculating projection data for the first reconstruction image, by using the first reconstruction image; and reconstructing a tomography image of the object by using the calculated projection data.

According to another aspect of an exemplary embodiment, there is provided a non-transitory computer readable recording medium having recorded thereon a program for executing the method.

According to another aspect of an exemplary embodiment, an apparatus for reconstructing a tomography image of an object from a plurality of projection images generated by scanning the object in a plurality of projection directions includes: a determination unit that determines whether a truncated portion of the object exists in each of the plurality of projection images; a first reconstruction unit that reconstructs a first reconstruction image by using at least one projection image, in which a truncated portion of the object does not exist, based on a result of the determining; a calculation unit that calculates projection data for the first reconstruction image, by using the first reconstruction image; and a second reconstruction unit that reconstructs a tomography image of the object by using the calculated projection data.

According to exemplary embodiments, since image distortion of a truncation boundary does not occur, the accuracy of a tomography image of the object may be improved.

BRIEF DESCRIPTION OF THE DRAWINGS

The above and/or other aspects will become more apparent by describing certain exemplary embodiments, with reference to the accompanying drawings, in which.

DETAILED DESCRIPTION

Certain exemplary embodiments are described in greater detail below, with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

Figure 1A:
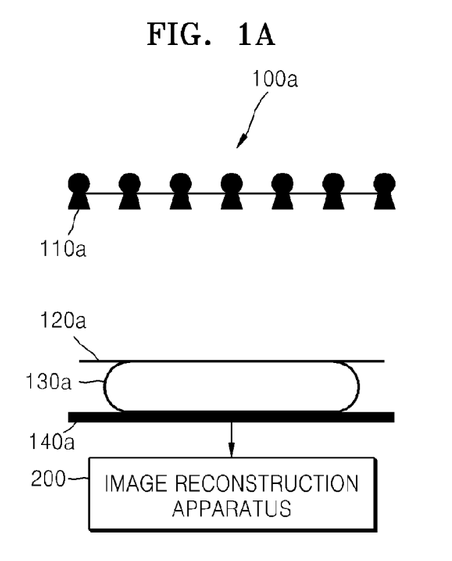
FIGS. 1A and 1B are diagrams illustrating tomography apparatuses according to an exemplary embodiment.
Figure 1B:
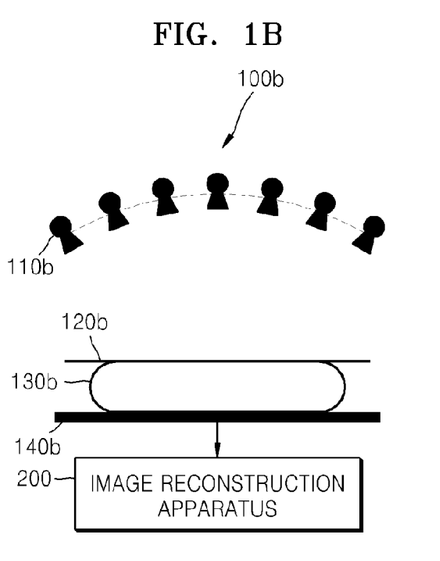

FIGS. 1A and 1B illustrate tomography apparatuses 100*a* and 100*b*, respectively, according to an exemplary embodiment. Referring to FIGS. 1A and 1B, each of the tomography apparatuses 100*a* and 100*b* includes a radiation source 110*a* or 110*b*, a compressor 120*a* or 120*b*, a detector 140*a* or 140*b*, and an image reconstruction apparatus 200. Although in FIGS. 1A and 1B, each of the detectors 140*a* and 140*b* and the image reconstruction apparatus 200 are illustrated as separate apparatuses, an exemplary embodiment is not limited thereto. That is, the detector 140*a* or 140*b* and the image reconstruction apparatus 200 may be implemented as an integrated single apparatus including a function of the detector 140a or 140b and a function of the image reconstruction apparatus 200.

Each of the tomography apparatuses 100a and 100b generates a tomography image of an object 130a or 130b. The tomography image may be a radiation image that is a tomography composition image of the object 130a or 130b, but an exemplary embodiment is not limited thereto. For example, the tomography image may be a three dimensional (3D) image, but an exemplary embodiment is not limited thereto.

In more detail, in the tomography apparatuses 100a and 100b, radiation that is emitted from the radiation source 110a or 110b passes through the object 130a or 130b, and the detector 140a or 140b detects a signal generated as the radiation passes through the object 130a or 130b, and generates a plurality of projection images. The image reconstruction apparatus 200 reconstructs the tomography image of the object 130a or 130b by using the plurality of projection images. The radiation emitted from the radiation source 110a or 110b may be X-rays, but an exemplary embodiment is not limited thereto.

The object 130a or 130b may be a breast of a human body. For example, the tomography apparatuses 100a and 100b may generate a tomography image of the object 130a or 130b in a state in which the object 130a or 130b has been compressed by using the compressor 120a or 120b. Thus, the tomography image generated by the tomography apparatuses 100a and 100b may be a Digital Breast Tomography (DBT) image.

The tomography apparatuses 100a and 100b may include various kinds of radiation sources. For example, the tomography apparatuses 100a and 100b may include the radiation source 110a that linearly moves or the radiation source 110b that moves in a circular arc, but an exemplary embodiment is not limited thereto.

The tomography apparatuses 100a and 100b may generate the plurality of projection images as the radiation radiated from the radiation source 110a or 110b that moves linearly or in the circular arc scans the object 130a or 130b in a plurality of projection directions. For example, the plurality of projection directions may be determined according to a movement direction of the radiation source 110a or 110b.

The plurality of projection directions may indicate directions of the radiation that is emitted to scan the object 130a or 130b. The plurality of projection directions may include a plurality of projection angles, which may indicate angles between the coordinates of the center of the detector 140a or 140b and a location of the radiation source 110a or 110b that emits the radiation toward the object 130a or 130b.

Thus, the tomography apparatuses 100a and 100b may generate at least one tomography image by reconstructing the plurality of projection images detected by the detector 140a or 140b, in the image reconstruction apparatus 200.

Figure 2:
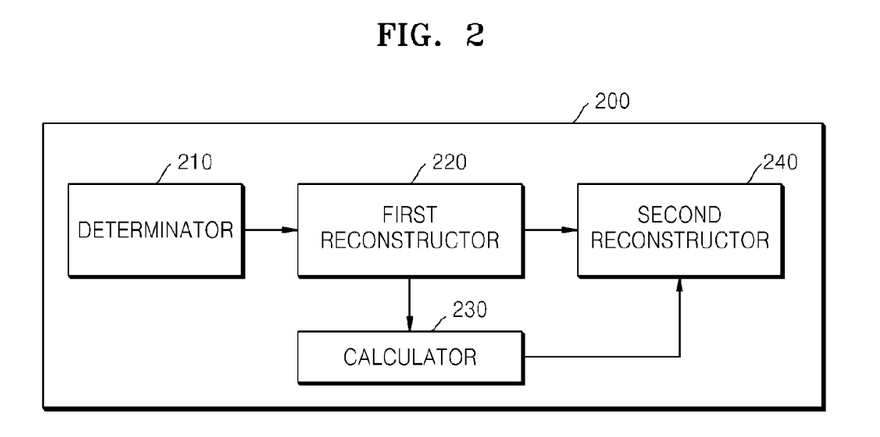
FIG. 2 is a block diagram of an image reconstruction apparatus according to an exemplary embodiment.

FIG. 2 is a block diagram of the image reconstruction apparatus 200 according to an exemplary embodiment. Referring to FIG. 2, the image reconstruction apparatus 200 includes a determinator 210, a first reconstructor 220, a calculator 230, and a second reconstructor 240.

In FIG. 2, the image reconstruction apparatus 200 includes only elements related to the current exemplary embodiment. However, it should be understood that other elements besides the elements illustrated in FIG. 2 may be further included in the image reconstruction apparatus 200.

The image reconstruction apparatus 200 illustrated in FIG. 2 may correspond to one processor or a plurality of processors. In addition, the determinator 210, the first reconstructor 220, the calculator 230, and the second reconstructor 240, which are included in the image reconstruction apparatus 200, may correspond to a single processor or a plurality of processors. The single processor or the plurality of processors may be implemented with an array including a plurality of logic gates, and may be implemented with a combination of a general purpose microprocessor and a memory in which a program executable in the general purpose microprocessor has been stored. It should be understood that the single processor or the plurality of processors may be implemented with hardware or software having another form.

The image reconstruction apparatus 200 reconstructs a tomography image of an object from a plurality of projection images generated by scanning the object in a plurality of projection directions.

The determinator 210 determines whether a portion in which the object is truncated (hereinafter, referred to as "a truncated portion of the object") exists in one of the plurality of projection images. However, this is not limiting and the determinator 210 may determine whether a truncated portion of the object is present in any number of the projection images, such as two, three, four, etc., including each of the projection images.

For example, a truncated portion of the object may be present in a projection image when the imaged object shown in a projection image is damaged, a portion of the imaged object shown in a projection image is lost, and the like.

In more detail, since the size of the detector 140a or 140b illustrated in FIGS. 1A and 1B is limited to a particular area, a truncated portion of the object may be present in a projection image. As another example, when the size of the object 130a or 130b illustrated in FIGS. 1A and 1B is relatively large, a portion of an imaged object may be cut off from a projection image and, thus, a truncated portion of the object may be present in a projection image. This will be described in detail with reference to FIG. 3.

The determinator 210 determines that a truncated portion of the object exists in a projection image when the data indicating the presence of the object unexpectedly appears or discontinues at some point in the projection image. This will be described in detail with reference to FIG. 4.

The first reconstructor 220 reconstructs a first reconstruction image by using at least one projection image, in which a truncated portion of the object is absent, based on a result of the determining by the determinator 210.

For example, the first reconstructor 220 reconstructs the first reconstruction image from one of more projection images, in which a truncated portion of the object is absent, by using an iterative algorithm. The iterative algorithm may include an algebraic reconstruction technique, an expectation maximization technique, or a compressive sensing-based technique, but an exemplary embodiment is not limited thereto.

Thus, since the first reconstruction image is reconstructed by using only projection images in which a truncated portion of the object is absent, an image free of a distortion of the object due to truncation may be reconstructed.

The calculator 230 calculates projection data for the first reconstruction image by using the first reconstruction image reconstructed by the first reconstructor 220. For example, the calculator 230 may calculate the projection data by performing a projection operation using a vector on the first reconstruction image.

For example, calculating the projection data for the first reconstruction image in the calculator 230 may include performing a forward projection on the first reconstruction image. However, an exemplary embodiment is not limited thereto.

For example, based on a projection direction for each of the truncated projection images, in which a truncated portion of the object exists, the calculator 230 may calculate projection data corresponding to each of the projection images in which a truncated portion of the object exists. Thus, the projection data calculated in the calculator 230 may be calculated by being projected in the same projection direction as a corresponding truncated projection image.

An example is described below for the case where a truncated portion of the object is present in first and second projection images, the first projection image is generated by scanning the object in a first projection direction, and the second projection image is generated by scanning the object in a second projection direction.

The calculator 230 calculates a first projection data of an image onto which the first reconstruction image has been projected in the first projection direction and calculates a second projection data of an image onto which the first reconstruction image has been projected in the second projection direction.

In more detail, the calculator 230 calculates projection data based on a projection operation for the first reconstruction image based on the assumption that there is a virtual detector for detecting a detection signal for a truncated portion of the object. This will be described in more detail with reference to FIG. 5.

The second reconstructor 240 reconstructs a tomography image of the object by using the projection data calculated by the calculator 230. For example, the reconstructed tomography image may be a tomography composition image. However, an exemplary embodiment is not limited thereto. For example, the second reconstructor 240 may generate a tomography image by using the iterative algorithm as described above with respect to the first reconstructor 220.

The second reconstructor 240 may reconstruct a tomography image by using the projection data calculated in the calculator 230 and at least one selected from a group consisting of a plurality of projection images, at least one projection image, in which a truncated portion of the object is absent, and the first reconstruction image reconstructed in the first reconstructor 220.

In an example described below, the determinator 210 has determined that a truncated portion of the object is present in first, second, ninth, and tenth projection images from among the first through tenth projection images. The first reconstructor 220 reconstructs the first reconstruction image by using the third through eighth projection images. The calculator 230 calculates first, second, ninth, and tenth projection data corresponding to the first, second, ninth, and tenth projection images by using the first reconstruction image.

For example, when the second reconstructor 240 reconstructs a tomography image by using a plurality of projection images and projection data, the second reconstructor 240 reconstructs the tomography image by using the first, second, ninth, and tenth projection data calculated in the calculator 230 and the first through tenth projection images.

As another example, when the second reconstructor 240 reconstructs a tomography image by using the first reconstruction image, a plurality of projection images, and the projection data, the second reconstructor 240 reconstructs the tomography image by using the first, second, ninth, and tenth projection data calculated in the calculator 230, the first reconstruction image, and the first through tenth projection images.

However, an exemplary embodiment is not limited thereto, and the second reconstructor 240 may reconstruct a tomography image by using the projection data and at least one projection image, in which a truncated portion of the object does not exist, and the first reconstruction image.

For example, the second reconstructor 240 reconstructs a tomography image by using the first, second ninth, and tenth projection data, and the third through eighth projection images.

As another example, the second reconstructor 240 may reconstruct a tomography image by using the first, second ninth, and tenth projection data, and the first reconstruction image reconstructed in the first reconstructor 220.

As another example, the second reconstructor 240 may reconstruct a tomography image by using the first, second ninth, and tenth projection data, the third through eighth projection images, and the first reconstruction image.

Thus, the second reconstructor 240 may reconstruct a tomography image having improved accuracy by using the calculated projection data, and at least one of the first reconstruction image previously reconstructed and at least one of the plurality of projection images.

For example, the second reconstructor 240 may estimate truncation data representing a truncated portion of the object with respect to at least one projection image, in which a truncated portion of the object exists, by using the projection data calculated in the calculator 230, and may reconstruct a tomography image of the object by using the estimated truncation data. This will be described in more detail with reference to FIG. 6.

Accordingly, since the image reconstruction apparatus 200 calculates projection data by using projection images in which a truncated portion of the object does not exist and reconstructs a tomography image by using the calculated projection data, the image reconstruction apparatus 200 may generate a tomography image having improved accuracy.

Since a tomography image may be distorted when reconstructing the tomography image by using projection images in which a truncated portion of the object exists, the image reconstruction apparatus 200 may reconstruct a tomography image by using only projection images in which a truncated portion of the object does not exist.

In detail, the calculator 230 calculates projection data for the first reconstruction image reconstructed by using only the projection images in which a truncated portion of the object does not exist. The second reconstructor 240 does not directly reconstruct the projection images in which a truncated portion of the object exists, but rather uses the projection data calculated in the calculator 230. Thus, the accuracy of a reconstructed tomography image may be improved. Accordingly, it is possible to prevent a phenomenon in which a distortion of an image occurs at the truncation boundary in a tomography image.

In addition, pixel values of images are influenced by a truncated portion of the object and increase a distorted contribution value of back projection as compared to an image in which a truncated portion of the object is absent, and, thus lower the accuracy and quality of a reconstructed image. Thus, since the image reconstruction apparatus 200 reconstructs a tomography image by using a reconstruction image reconstructed using only the projection images in which a truncated portion of the object is absent, the quality of the reconstructed tomography image may be substantially improved.

Figure 3:
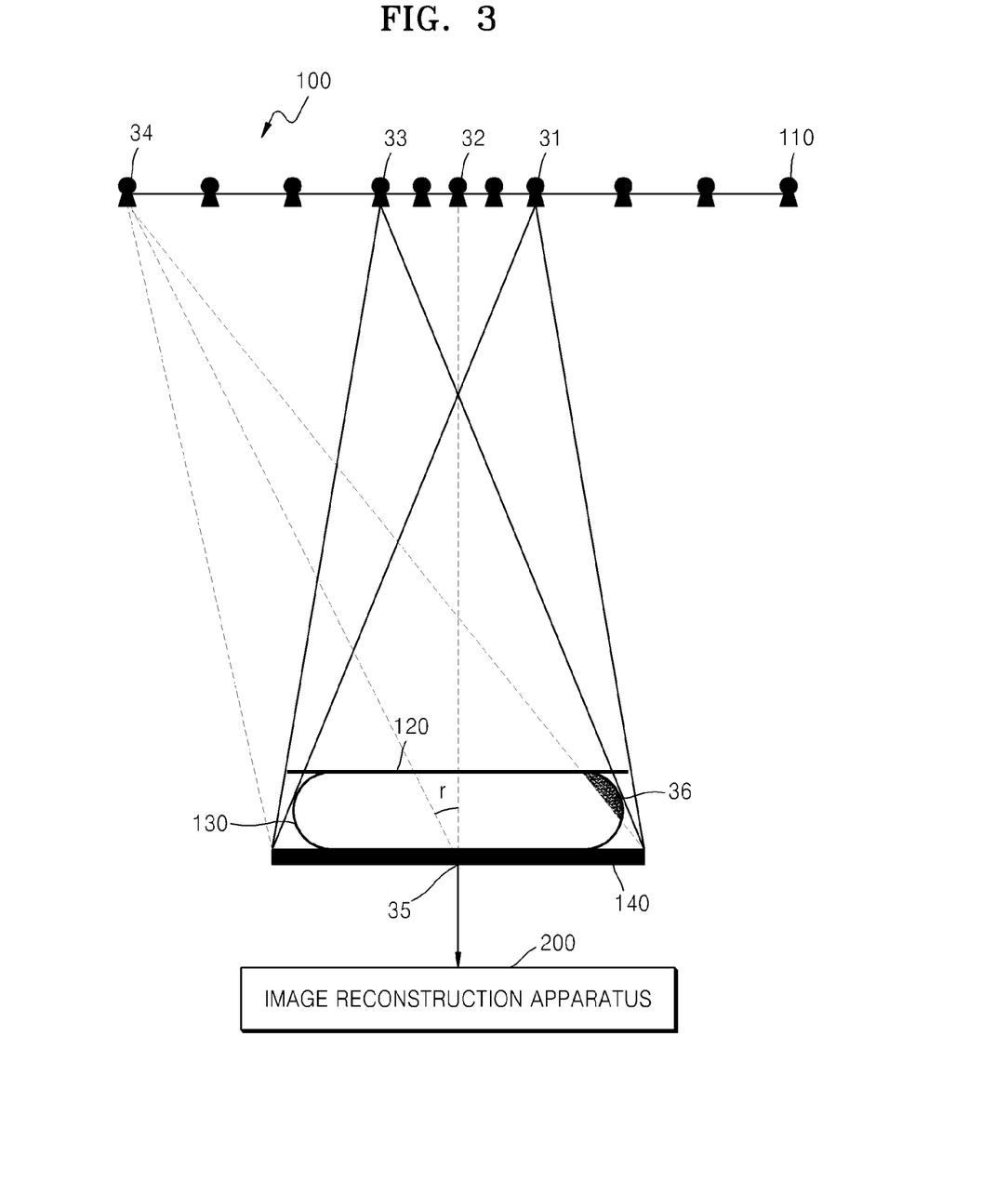
FIG. 3 is a diagram illustrating an example of a truncated portion of an object in a projection image, according to an exemplary embodiment.

FIG. 3 is a diagram illustrating an example of a truncated portion of the object in a projection image, according to an exemplary embodiment. Referring to FIG. 3, a tomography apparatus 100 includes a radiation source 110, a compressor 120, a detector 140, and an image reconstruction apparatus 200.

In FIG. 3, for convenience of description, a case where the radiation source 110 of the tomography apparatus 100 moves linearly is described. However, an exemplary embodiment is not limited thereto.

As X-rays radiated from the linearly moving radiation source 110 scan an object 130 compressed by the compressor 120 in a plurality of projection directions, a plurality of projection images may be generated. The plurality of projection directions may be determined according to a moving direction of the radiation source 110.

However, some of the plurality of projection images may be projection images in which a truncated portion of the object exists, according to the location of the radiation source 110 that radiates the X-rays to the object 130.

For example, as the radiation source 110 moves further away from the central position of the linear movement of the radiation source 110, i.e., a first position 32, the probability that a truncated portion of the object exists in a projection image becomes higher.

As another example, as the radiation source 110 moves, the larger an absolute value of an angle r between the radiation source 110 and the center axis 35 of a coordinate system, the higher the probability that a truncated portion of the object exists in a projection image. For example, when the absolute value of an angle between the radiation source 110 and the center axis 35 of the coordinate system is equal to or greater than approximately 27°, a truncated portion of the object may exist in a projection image. However, an exemplary embodiment is not limited thereto.

Referring to FIG. 3, when the linearly moving radiation source 110 is located between a second position 31 and a third position 33, a truncated portion of the object does not exist in corresponding first and second projection images.

On the other hand, when the linearly moving radiation source 110 is located in a fourth position 34, a truncated portion 36 of the object is not included in a third projection image and, thus, a truncated portion exists in the third projection image.

In this manner, when the size of the detector 140 is limited, a truncated portion of the object may be present in a projection image. However, there might be other instances when a truncated portion of the object may be present in a projection image. For example, when the size of the object 130 is relatively large, a projection image may include a truncated portion of the object. As another example, when a beam width of the radiation source 110 does not include the whole area of the object 130, a projection image may include a truncated portion of the object.

Figure 4:
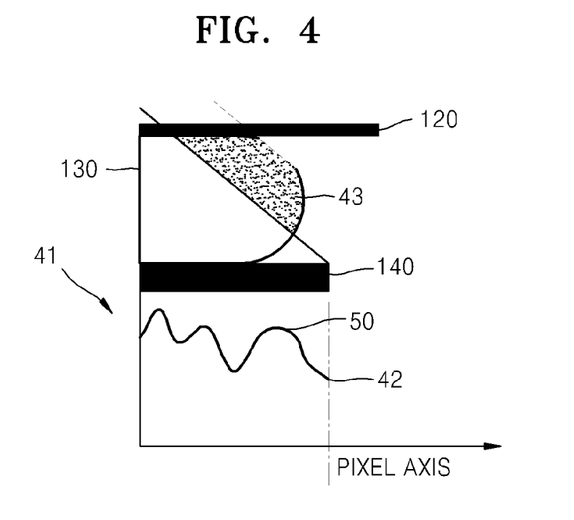
FIG. 4 is a diagram illustrating an example of determining whether a truncated portion of the object exists in a projection image.

FIG. 4 is a diagram illustrating an example of a method in which the determinator 210 illustrated in FIG. 2 determines whether a truncated portion of the object exists in a projection image. Referring to a graph 41 of a detection signal illustrated in FIG. 4, as the object 130 compressed by the compressor 120 is scanned, the detector 140 may detect a detection signal 50 according to a pixel axis. The detection signal 50 detected by the detector 140 may be data indicating the presence of the object 130.

The determinator 210 refers to the detection signal 50 detected by the detector 140 and determines that a truncated portion 43 of the object is not included in the data, and, thus, a truncated portion exists in a projection image when the data indicating the presence of the object 130 suddenly discontinues at or after a first truncation position 42.

In more detail, the determinator 210 may determine whether a truncated portion of the object exists in a projection image by referring to start and end portions of the data indicating the presence of the object 130 in the projection image.

That is, the determinator 210 may determine that a portion of the object is absent in a projection image when the data indicating the presence of the object, detected by the detector 140, suddenly discontinues at a first truncation position 42 at the end portion of the data or when the data which is expected to indicate the presence of the object does not exist prior to a second truncation position (not shown) at the start portion of the data.

Alternatively, the determinator 210 may determine whether a truncated portion 43 of the object exists in a projection image, based on an arithmetic calculation result obtained by using a thickness of the object, which may be estimated by a location of the compressor 120, a previously known size of the detector 140, a location of the detector 140 when the detector 140 moves, a location of the radiation source 110, and a direction and width of a beam that is radiated from the radiation source 110.

Accordingly, the determinator 210 may accurately determine whether a truncated portion 43 of the object exists in a projection image by using at least one from the above-discussed methods.

Figure 5:
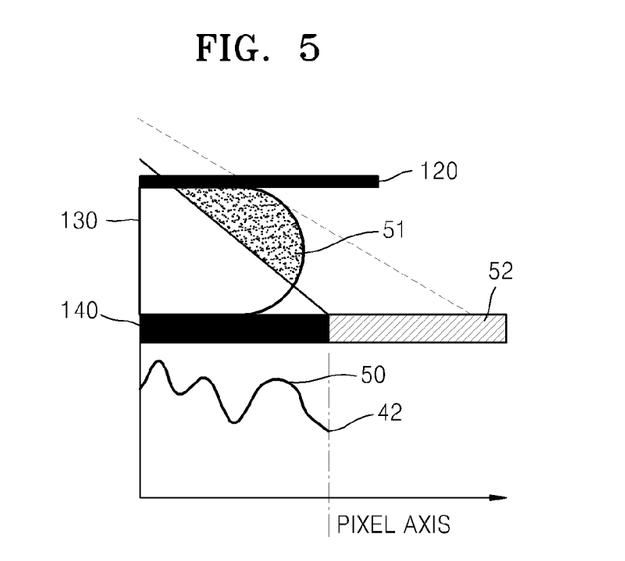
FIG. 5 is a diagram illustrating an example of calculating projection data based on a projection operation.

FIG. 5 is a diagram illustrating an example of a method in which the calculator 230 illustrated in FIG. 2 calculates projection data based on a projection operation.

Referring to FIG. 5, the calculator 230 calculates projection data based on a projection operation using a vector or the like with respect to the first reconstruction image based on the assumption that a virtual detector 52 detects a detection signal for a truncated portion 51 of the object. In this case, the projection data calculated by the calculator 230 with respect to the first reconstruction image may include the data of the truncated portion 51 of the object.

Thus, the calculator 230 may calculate the projection data for the first reconstruction image in consideration of the presence of the virtual detector 52, and in this case, the calculated projection data does not include the truncated portion of the object.

Figure 6:
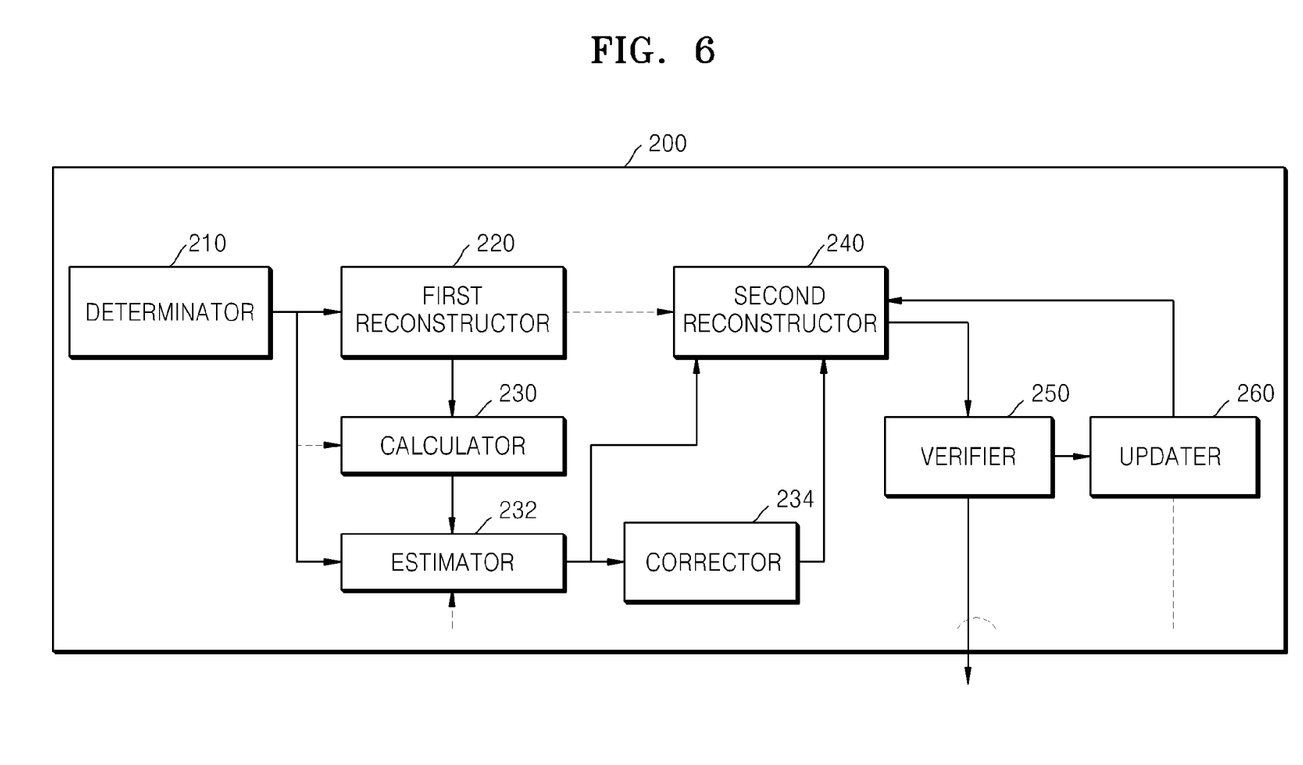
FIG. 6 is a block diagram of an image reconstruction apparatus according to an exemplary embodiment.

FIG. 6 is a block diagram of an image reconstruction apparatus 200 according to an exemplary embodiment. Referring to FIG. 6, the image reconstruction apparatus 200 includes a determinator 210, a first reconstructor 220, a calculator 230, an estimator 232, a corrector 234, a second reconstructor 240, a verifier 250, and an updater 260.

In FIG. 6, the image reconstruction apparatus 200 includes only elements related to the current exemplary embodiment. However, it should be understood that other elements besides the elements illustrated in FIG. 6 may be further included in the image reconstruction apparatus 200.

The image reconstruction apparatus 200 illustrated in FIG. 6 corresponds to the image reconstruction apparatus 200 described above with reference to FIG. 2. Thus, the described above with reference to FIG. 2 may be applied to the image reconstruction apparatus 200 illustrated in FIG. 6, and a repeated description will be omitted.

The image reconstruction apparatus 200 illustrated in FIG. 6 may correspond to one processor or a plurality of processors. In addition, the determinator 210, the first reconstructor 220, the calculator 230, the estimator 232, the corrector 234, the second reconstructor 240, the verifier 250, and the updater 260, which are included in the image reconstruction apparatus 200, may correspond to one processor or a plurality of processors.

The image reconstruction apparatus 200 reconstructs a tomography image of an object from a plurality of projection images generated by scanning the object in a plurality of projection directions.

The determinator 210 determines whether a truncated portion of the object exists in the plurality of projection images. The first reconstructor 220 reconstructs a first reconstruction image by using at least one projection image, in which a truncated portion of the object does not exist, based on a result of the determining by the determinator 210. The calculator 230 calculates projection data for the first reconstruction image, by using the first reconstruction image reconstructed by the first reconstructor 220.

The estimator 232 estimates truncation data representing a truncated portion of the object with respect to one or more of the truncated projection images, in which a truncated portion of the object exists, by using the projection data calculated in the calculator 230.

Based on a projection direction for each of the truncated projection images, the calculator 230 may calculate projection data corresponding to each of the truncated projection images. The estimator 232 estimates the truncation data for each of the truncated projection images, by using the projection data corresponding to each of the truncated projection images.

In an example described below, a truncated portion of the object is present in first and second truncated projection images and the calculator 230 calculates first projection data corresponding to the first truncated projection image and second projection data corresponding to the second truncated projection image.

The estimator 232 estimates first truncation data representing a truncated portion of the object by using the first projection data calculated in the calculator 230. For example, the estimator 232 may compare the first projection data and the first truncated projection image and may estimate first truncation data representing a truncated portion of the object, according to a result of the comparing.

For example, when a truncated portion of the object exists in the first truncated projection image, the first truncated projection image includes a first truncation position 42 at or after which data indicating the presence of the object is suddenly discontinued. Since the data detected before the first truncation position 42 is substantially similar to the data of the truncated portion, the estimator 232 may estimate the first truncation data for the first truncated portion, with reference to the first projection data detected before the first truncation position 42.

For example, the estimator 232 may estimate second truncation data representing a truncated portion of the object by using the second projection data calculated in the calculator 230 similarly to what is described above with respect to the first truncation data.

The corrector 234 corrects the truncation data estimated in the estimator 232 by using a sum of intensity values of one of the projection images in which a truncated portion of the object is absent and a sum of intensity values of a truncated projection image corresponding to the truncation data estimated in the estimator 232.

The sum of the intensity values of the projection image may be the amount of energy detected by a detector from radiation passing through the object.

For example, when a truncated portion of the object is present in first, second, ninth, and tenth projection images from among the first through tenth projection images, the estimator 232 estimates first, second, ninth, and tenth truncation data corresponding to the first, second, ninth, and tenth projection images.

The corrector 234 may correct the first truncation data by using a sum of intensity values of any one of the third through eight projection images and a sum of intensity values of the first truncated projection image. The corrector 234 may correct the second, ninth, and tenth truncation data in the similar manner.

For example, the corrector 234 corrects scaling errors in the truncation data estimated in the estimator 232 by subtracting the sum of intensity values of the truncated projection image corresponding to the truncation data estimated in the estimator 232 from the sum of intensity values of one of the projection images in which a truncated portion of the object does not exist.

In more detail, when radiation energy output from a radiation source passes through the object, the amount of radiation that is attenuated in the object is relatively constant regardless of the location of the radiation source. Thus, the sum of intensity values of each of a plurality of projection images generated as radiation passes through the object is constant. That is, data consistency is achieved.

However, when a truncated projection image is generated, the sum of intensity values of the truncated projection image is not equal to that of a projection image in which a truncated portion of the object is absent.

Thus, the corrector 234 corrects scaling errors in the truncation data estimated in the estimator 232 by subtracting the sum of intensity values of the truncated projection image corresponding to the truncation data estimated in the estimator 232 from the sum of intensity values of one of the projection images in which a truncated portion of the object is absent. This will be described in more detail with reference to FIGS. 7A and 7B below.

The second reconstructor 240 reconstructs a tomography image of the object by using the projection data calculated in the calculator 230. For example, the second reconstructor 240 may reconstruct a tomography image of the object by using the truncation data corrected in the corrector 234.

For example, the second reconstructor 240 may reconstruct a tomography image of the object by reflecting the corrected truncation data in a truncated projection image in which a truncated portion of the object exists.

As another example, the second reconstructor 240 may reconstruct a tomography image of the object by reflecting the corrected truncation data in the projection data calculated by using the first reconstruction image.

Thus, the accuracy of a tomography image reconstructed in the second reconstructor 240 may be improved.

For example, the image reconstruction apparatus 200 may perform a verification operation with respect to a tomography image reconstructed in the second reconstructor 240.

The verifier 250 calculates an error between verification data and a plurality of projection images generated by scanning the object in the plurality of projection directions. In the verification operation, the verifier 250 excludes the truncation data which corresponds to a truncated portion of the object, from the projection data of images onto which a tomography image reconstructed in the second reconstructor 240 has been projected in a plurality of projection directions. Then, the verifier 250 verifies whether the calculated error satisfies a predetermined condition.

In more detail, the verifier 250 may calculate projection data of a tomography image by performing a projection operation using a vector on a tomography image reconstructed in the second reconstructor 240. For example, calculating the projection data by the verifier 250 includes performing a forward projection. However, an exemplary embodiment is not limited thereto. The verifier 250 may calculate the verification data by excluding the truncation data corresponding to a truncated portion of the object from the projection data generated for the tomography image.

For example, in the case where a truncated portion of the object exists in a projection image corresponding to first projection direction of first through tenth projection directions, the verifier 250 calculates first through tenth projection data corresponding to the first through tenth projection directions with respect to a tomography image. Then, the verifier 250 calculates verification data while excluding the truncation data, which corresponds to a truncated portion of the object, from the first projection data corresponding to the first projection direction, in which a truncated portion of the subject exists. Thus, the verification data may include data, other than the truncation data, from the first projection data and the second through tenth projection data.

Accordingly, when a plurality of projection images generated by scanning the object in a plurality of projection images include a truncated portion of the object, the verifier 250 compares the data, other than the truncation data, of the projection data generated for a tomography image with the plurality of projection images.

The verifier 250 calculates an error between the calculated verification data and the plurality of projection images generated by scanning the object in the plurality of projection directions, and verifies whether the calculated error satisfies a predetermined condition.

For example, the error may be calculated by comparing a projection image with verification data, of which a projection direction is the same as that of the projection image, for every pixel. For example, the error may be calculated by comparing the first projection image generated by scanning the object in the first projection direction with the first projection data calculated by performing projection operation on a tomography image in the first projection direction for every pixel. However, an exemplary embodiment is not limited thereto.

The predetermined condition may indicate whether the error is less than a predetermined reference value or whether the error converges to a predetermined value. However, an exemplary embodiment is not limited thereto.

Thus, the verifier 250 outputs a reconstructed tomography image as a verified tomography image when the error is less than the predetermined reference value or when the error converges to the predetermined value.

For example, the verifier 250 controls the updater 260 to update projection data for a tomography image when the error is greater than the predetermined reference value or when the error does not converge to the predetermined value.

The updater 260 updates projection data for a tomography image, which has been calculated in the verifier 250, by using the error calculated in the verifier 250 when the error does not satisfy the predetermined condition as a result of a verification by the verifier 250.

For example, the updater 260 may update projection data for a tomography image, which has been calculated in the verifier 250, by subtracting the error calculated in the verifier 250 from the projection data for the tomography image. The updater 260 may also update projection data for a tomography image, which has been calculated in the verifier 250, by applying a suitable weight to the error calculated in the verifier 250 and subtracting the weighted error from the projection data for the tomography image.

The weight may be a value for adjusting a scaling factor with respect to the error, and, for example, may be 0.1. However, an exemplary embodiment is not limited thereto. For example, the weight may be differently set between truncation data estimated with respect to a truncated portion of the object and the data other than the truncation data from among projection data for a tomography image. However, an exemplary embodiment is not limited thereto.

For example, the updater 260 may perform additional image processing for improving the quality of the tomography image. For example, the updater 260 may perform noise reduction, quality restoration, total variation minimization, and the like. However, an exemplary embodiment is not limited thereto.

Thus, the second reconstructor 240 may reconstruct again a tomography image of the object by using projection data updated in the updater 260.

The image reconstruction apparatus 200 may allow operations of the estimator 232, the corrector 234, and the second reconstructor 240 to be performed once again by using projection data updated in the updater 260. However, an exemplary embodiment is not limited thereto. For example, the estimator 232 may estimate truncation data indicating a truncated portion of the object with respect to at least one truncated projection image, by using projection data updated in the updater 260 instead of projection data calculated in the calculator 230. Thereafter, the corrector 234 and the second reconstructor 240 may perform the same operations as described above.

Operations of the verifier 250 and the updater 260 will now be described in more detail below. The verifier 250 verifies whether an error calculated by using verification data for a reconstructed tomography image is less than a predetermined reference value or whether the error converges to a predetermined value.

For example, the predetermined reference value may be set by a user or may be a value set by default.

As another example, the case when the error converges to a predetermined value will be described in more detail below.

As a result of verification by the verifier 250, if a first error calculated by using a first tomography image reconstructed in the second reconstructor 240 is greater than the predetermined reference value or does not converge to the predetermined value, the updater 260 may update projection data for the first tomography image and the second reconstructor 240 may reconstruct a second tomography image by using the updated projection data. However, depending on a usage environment, the image reconstruction apparatus 200 may reconstruct the second tomography image by performing operations of the estimator 232, the corrector 234, and the second reconstructor 240, respectively.

The verifier 250 may calculate a second error by using the second tomography image, and may determine whether the error converges to the predetermined value according to whether the second error value is similar or substantially equal to the first error value.

For example, the second error may be similar to the first error if a difference between the second error and the first error is equal to or less than a predetermined value, which may be set by a user or may be a value set by default.

Thus, the verifier 250 determines that the error converges to the predetermined value when the second error is similar to the first error, and thus outputs the second tomography image as a verified tomography image.

However, if as a result of verification by the verifier 250, the second error is not similar to the first error, the updater 260 may update projection data for the second tomography image, and the second reconstructor 240 may reconstruct a third tomography image by using the updated projection data. Depending on a usage environment, the image reconstruction apparatus 200 may reconstruct the third tomography image by performing operations of the estimator 232, the corrector 234, and the second reconstructor 240, respectively.

In this manner, since the verifier 250 performs a verification operation for a tomography image reconstructed in the second reconstructor 240, the image reconstruction apparatus 200 may generate a verified tomography image by repeatedly performing the above operations when an error of a tomography image does not satisfy a predetermined reference value.

Thus, since the image reconstruction apparatus 200 reconstructs a tomography image after performing a correction with respect to projection images in which a truncated portion of the object exists, the image reconstruction apparatus 200 may perform an accurate reconstruction and thus may generate a tomography image having improved accuracy.

Figure 7A:
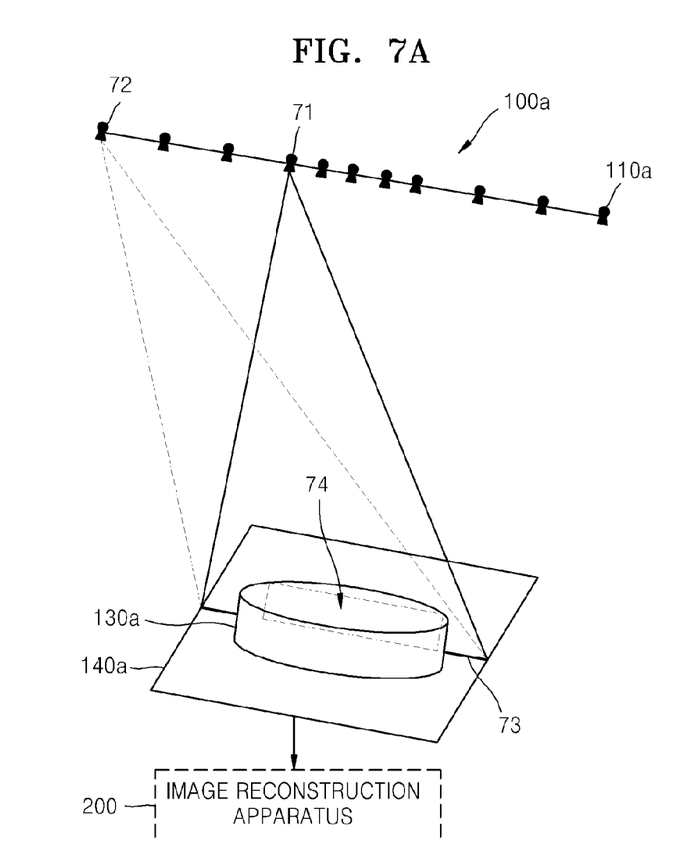
FIGS. 7A and 7B are diagrams illustrating correcting truncation data according to an exemplary embodiment.
Figure 7B:
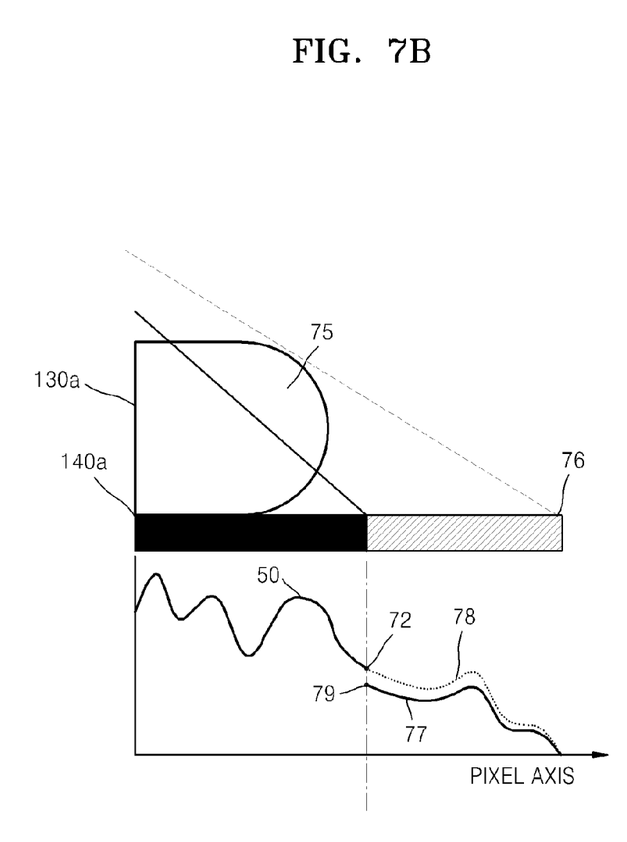

FIGS. 7A and 7B are diagrams illustrating a method of correcting truncation data in the corrector 234 illustrated in FIG. 6. Referring to FIG. 7A, a tomography apparatus 100a generates a tomography image for an object 130a and may include a linearly moving radiation source 110a, a detector 140a, and an image reconstruction apparatus 200.

In FIG. 7A, for convenience of explanation, a case where the radiation source 110a linearly moves is illustrated. However, an exemplary embodiment is not limited thereto.

In order to generate a tomographic image of the object 130a, the radiation source 110a included in the tomography apparatus 100a scans the object 130a while linearly moving.

Thus, the radiation emitted from the radiation source 110a is attenuated in the object 130a and is input to the detector 140a after passing through the object 130a. The detector 140a may generate a plurality of projection images depending on a location of the radiation source 110a by detecting a signal passing through the object 130a.

If the radiation is emitted from the radiation source 110a toward the object 130a, the energy of the radiation emitted toward the object 130a is attenuated in the object 130a depending on a radiation attenuation coefficient of the object 130a, and then the radiation emitted toward the object 130a is input to the detector 140a after passing through the object 130a.

Thus, the amount of the radiation energy that is attenuated in the object 130a may be calculated by using the radiation attenuation coefficient of the object 130a with respect to the radiation that is emitted toward the object 130a. When the radiation is emitted toward the object 130a, a surface integral value of the radiation attenuation coefficient with respect to a cross section 74 of the object 130a through which the radiation passes may be the amount of energy attenuated in the object 130a. The cross section 74 of the object 130a through which the radiation passes may be a cross section that is formed by a linear scan line along which the radiation source 110a moves and a line 73 of the detector 140a, which is parallel with the linear scan line.

The amount of energy that has passed through the object 130a may be a sum of intensity values of a projection image generated as the radiation passes through the object 130a. The radiation that has passed through the object 130a may be detected in the detector 140a and a detection signal detected in the detector 140a may appear as a projection image.

When radiation energy output from the radiation source 110a passes through the object 130a, the amount of radiation that is attenuated in the object 130a is relatively constant regardless of the location of the radiation source 110a. Thus, a sum of intensity values of each of a plurality of projection images generated as the radiation passes through the object 130a is nearly constant.

However, when a truncated projection image, in which a truncated portion of the object exists, is generated, a sum of intensity values of a truncated projection image is not equal to that of a projection image in which a truncated portion of the object is absent.

For example, the sum of intensity values of the first projection image generated by passing radiation through the object 130a as the radiation source 110a emits the radiation from a first position 71 toward the object 130a is equal to that of a second projection image generated by passing radiation through the object 130a as the radiation source 110a emits the radiation from a second position 72 toward the object 130a.

However, when a truncated projection image in which a truncated portion of the object exists is generated according to a location of the radiation source 110a, the sum of intensity values of a truncated projection image generated by passing the radiation through the object 130a is less than that of a projection image in which a truncated portion of the object 130a is absent.

Thus, the corrector 234 may calculate the amount of energy corresponding to the truncated portion 75 of the object 130a by subtracting the sum of intensity values of the truncated projection image corresponding to the truncation data estimated in the estimator 232 from the sum of intensity values of any one of the projection images in which a truncated portion of the object is absent. The amount of energy corresponding to the truncated portion 75 of the object 130a may be a surface integral value of the radiation attenuation coefficient of the object 130a with respect to the truncated portion 75 of the object 130a.

The corrector 234 appropriately corrects scaling errors in truncation data 77 estimated in the estimator 232 by using the amount of energy corresponding to the truncated portion 75 of the object 130a. For example, the corrector 234 may correct scaling errors in the truncation data 77 by comparing the amount of energy corresponding to the truncated portion 75 of the object 130a with the amount of energy that is calculated by using the truncation data 77 estimated in the estimator 232.

For example, the corrector 234 may adjust the truncation data 77 so that an intensity value of a start point 79 of the truncation data 77 is equal to that of a position 72 where data is suddenly discontinued in a truncated projection image. Thus, the corrected truncation data 78 may be generated according to a result of a scaling correction that has been performed on the truncation data 77 estimated by using a virtual detector 76.

Figure 8:
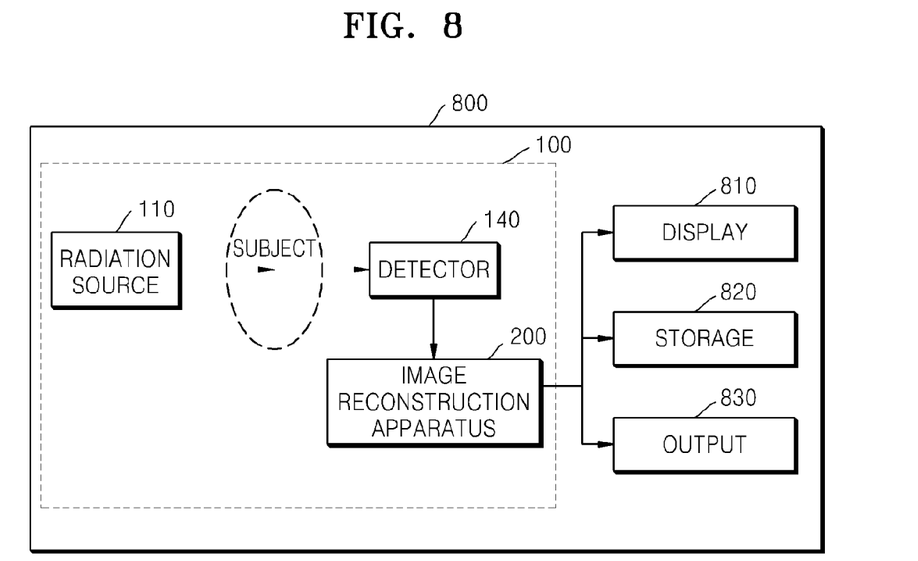
FIG. 8 is a diagram illustrating a medical imaging system according to an exemplary embodiment.

FIG. 8 is a diagram illustrating a medical imaging system 800 according to an exemplary embodiment. Referring to FIG. 8, the medical imaging system 800 includes a tomography apparatus 100, a display 810, a storage 820, and an output 830. The tomography apparatus 100 includes a radiation source 110, a detector 140, and an image reconstruction apparatus 200.

The tomography apparatus 100 and the image reconstruction apparatus 200 illustrated in FIG. 8 correspond to the tomography apparatus 100 and the image reconstruction apparatus 200, respectively, described above with reference to FIGS. 1, 2, and 6. Thus, contents described in relation to FIGS. 1, 2, and 6 may be applied to the tomography apparatus 100 and the image reconstruction apparatus 200 illustrated in FIG. 8, and thus, a detailed description thereof will be omitted.

In FIG. 8, the medical imaging system 800 includes only elements related to the exemplary current embodiment. However, it should be understood that other elements besides the elements illustrated in FIG. 8 may be further included in the medical imaging system 800.

The medical imaging system 800 may include an image diagnostic system using radiation, for example, X-rays. For example, the medical imaging system 800 may be a mammography image diagnostic system that is used for detecting a lesion of breast tissue consisting of soft tissues in the human body.

The tomography apparatus 100 generates a tomography image of an object.

The radiation source 110 emits radiation toward the object in a plurality of projection directions. For example, the radiation source 110 may emit the radiation toward the object in the plurality of projection directions while moving linearly or in a circular arc. However, an exemplary embodiment is not limited thereto, and a plurality of radiation sources may be arranged linearly or in a circular arc.

The detector 140 detects a signal generated as the radiation emitted from the radiation source 110 passes through the object, and generates a plurality of projection images corresponding to the plurality of projection directions.

The image reconstruction apparatus 200 reconstructs a first reconstruction image by using at least one projection image, in which a truncated portion of the object does not exist, calculates projection data for the first reconstruction image, and reconstructs a tomography image of the object by using the calculated projection data.

The display 810 displays the tomography image generated in the image reconstruction apparatus 200. For example, the display 810 includes output devices such as a display panel, a liquid crystal display (LCD) screen, or a monitor.

However, the medical imaging system 800 may lack the display 810 but may include an output 830 for outputting the tomography image generated in the image reconstruction apparatus 200 to an external display device (not shown).

The storage 820 stores data that is generated during an operation of the medical imaging system 800. The storage 820 may be a storage medium and may include a hard disk drive (HDD), a read only memory (ROM), a random access memory (RAM), a flash memory, or a memory card.

The output 830 may transmit or receive data to or from an external device through a wired or wireless network or wired serial communication. The wired or wireless network may include Internet, a local area network (LAN), a wireless local area network (Wireless LAN), a wide area network (WAN), a personal area network (PAN), or the like. However, an exemplary embodiment is not limited thereto, and the wired or wireless network may be any network capable of transmitting and receiving information.

For example, the storage 820 and the output 830 may be integrated as a picture archiving communication system (PACS) by further including an image interpretation and search function.

According to exemplary embodiments, the medical imaging system 800 may accurately reconstruct a tomography image of the object without a distortion caused by a truncated portion of the object.

Figure 9:
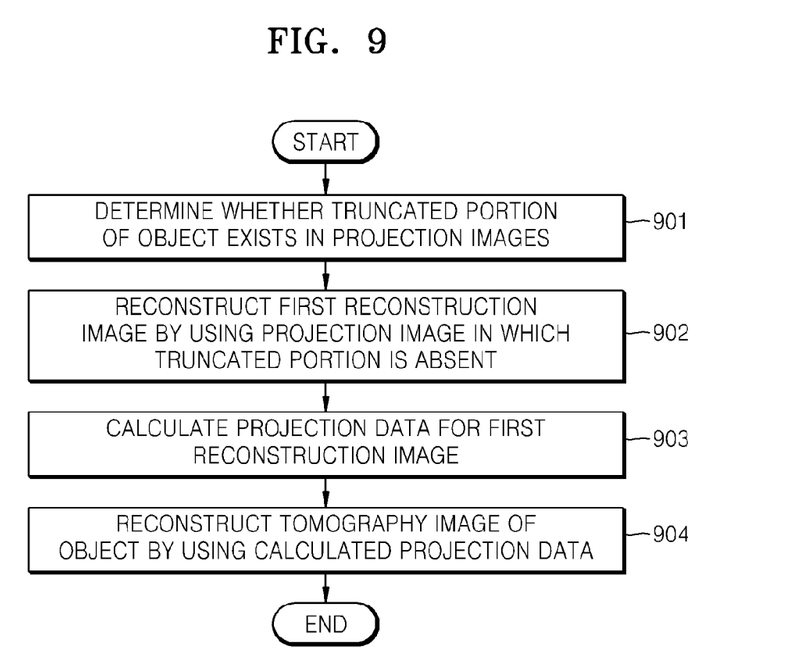
FIG. 9 is a flowchart illustrating a method of reconstructing a tomography image, according to an exemplary embodiment.

FIG. 9 is a flowchart illustrating a method of reconstructing a tomography image, according to an exemplary embodiment. Referring to FIG. 9, the method of reconstructing a tomography image includes operations that are sequentially processed in the tomography apparatus 100, image reconstruction apparatus 200, and medical imaging system 800 illustrated in FIGS. 1, 2, 6, and 8. Thus, although omitted below, contents described above in relation to the tomography apparatus 100, the image reconstruction apparatus 200, and the medical imaging system 800 illustrated in FIGS. 1, 2, 6, and 8 may be applied to the method of reconstructing a tomography image.

In operation 901, the determinator 210 determines whether a truncated portion of an object exists in at least one of a plurality of projection images which are generated by scanning the object in a plurality of projection directions.

In operation 902, the first reconstructor 220 reconstructs a first reconstruction image by using at least one projection image, in which a truncated portion of the object does not exist, based on a result of the determining in operation 901.

In operation 903, the calculator 230 calculates projection data for the first reconstruction image, by using the first reconstruction image reconstructed in operation 902.

In operation 904, the second reconstructor 240 reconstructs a tomography image of the object by using the projection data calculated in operation 903.

In this manner, a tomography image having improved accuracy may be reconstructed by performing an exemplary tomography image reconstruction method.

Figure 10:
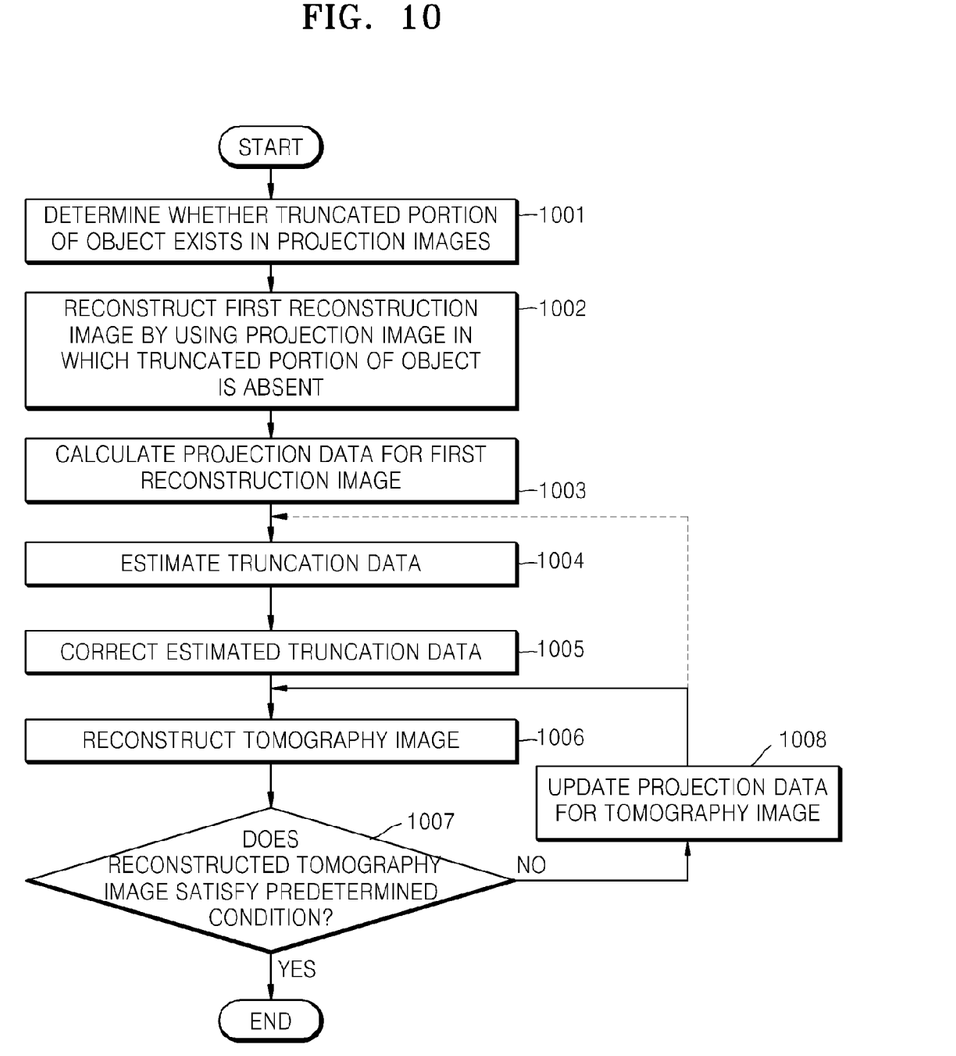
FIG. 10 is a flowchart illustrating a method of reconstructing a tomography image, according to an exemplary embodiment.

FIG. 10 is a flowchart illustrating a method of reconstructing a tomography image, according to an exemplary embodiment. Referring to FIG. 10, the tomography image reconstruction method of FIG. 10 includes operations that are sequentially processed in the tomography apparatus 100, the image reconstruction apparatus 200, and the medical imaging system 800 illustrated in FIGS. 1, 2, 6, and 8. Thus, although omitted below, contents described above in relation to the tomography apparatus 100, the image reconstruction apparatus 200, and the medical imaging system 800 illustrated in FIGS. 1, 2, 6, and 8 may be applied to the tomography image reconstruction method of FIG. 10.

Operations 1001, 1002, and 1003 of FIG. 10 are substantially the same as operations 901, 902, and 903 of FIG. 9, and thus, an explanation thereof will not be repeated here.

In operation 1004, the estimator 232 estimates truncation data representing a truncated portion of an object with respect to at least one truncated projection image, by using projection data generated in operation 1003.

In operation 1005, the corrector 234 corrects the truncation data estimated in operation 1004 by using a sum of intensity values of at least one projection image in which a truncated portion of the object does not exist and a sum of intensity values of a truncated projection image corresponding to the estimated truncation data.

In operation 1006, the second reconstructor 240 reconstructs a tomography image of the object by using the truncation data corrected in operation 1005.

In operation 1007, the verifier 250 calculates an error by using the verification data other than the truncation data of the projection data of images, onto which a tomography image reconstructed has been projected in a plurality of projection directions, and a plurality of projection images generated by scanning the object in the plurality of projection directions. Then, the verifier 250 verifies whether the calculated error satisfies a predetermined condition.

Based on a verification result of operation 1007, when the calculated error satisfies the predetermined condition, the verifier 250 outputs the tomography image reconstructed in operation 1006 as a diagnostic image for the object.

Further operation 1008 may be performed when the calculated error does not satisfy the predetermined condition, as determined in operation 1007.

In operation 1008, the updater 260 updates projection data for the tomography image by using the error calculated in operation 1007 when the error does not satisfy the predetermined condition.

After the projection data has been updated in operation 1008, the second reconstructor 240 reconstructs again a tomography image of the object by using the updated projection data, in operation 1006. Next, operation 1007 may be repeated again.

However, an exemplary embodiment is not limited thereto. That is, operation 1004 may be performed after operation 1008, and the estimator 232 may estimate truncation data representing the truncated portion with respect to at least one truncated projection image, by using the projection data updated in operation 1008. After this, operation 1005 through operation 1007 may be repeated again.

For example, in operation 1007, the verifier 250 may determine whether a predetermined condition is satisfied according to whether the repetition processes as described above have been repeated an experimentally predetermined number of times, instead of the verification process for calculating the error.

For example, when operations 1004 through 1008 as described above are repeated three times, i.e., the predetermined number of repetitions, the verifier 250 may verify that the predetermined condition is satisfied.

As another example, when operations 1006 through 1008 as described above are repeated three times, i.e., the predetermined number of repetitions, the verifier 250 may verify that the predetermined condition is satisfied.

Thus, by performing the tomography image reconstruction method according to the current exemplary embodiment, a verified tomography image satisfying a predetermined condition may be reconstructed.

When reconstructing a tomography image by using the image reconstruction apparatus 200, the tomography apparatus 100, and/or the medical imaging system 800 according the current exemplary embodiment, a truncated portion of an object is estimated from projection images in which a truncated portion does not exist, and thus, accuracy may be improved compared to a correction method using pixel information of surrounding image. In addition, since a reconstruction image is reconstructed by using the projection images in which a truncated portion does not exist, projection data is calculated by projecting the reconstruction image, and truncation data corresponding to a truncated portion of the object is estimated based on the calculated projection data, the accuracy of a reconstructed tomography image may be improved.

In addition, the tomography image reconstruction method according to the current exemplary embodiment may be used as an algorithm for reconstructing a tomography image in a digital detector-based breast tomography composition system. Thus, although data truncation occurs during a tomography composition photographing process due to a limited size of a detector, a distortion phenomenon of a reconstructed tomography image may be prevented by using only an algorithm without changing hardware such as the movement of the detector.

When performing a wide angle scan in a digital detector-based breast tomography composition system, a truncation phenomenon of data may occur more frequently. In this case, by estimating truncation data and then correcting the estimated truncation data by using the tomography image reconstruction method according to the current exemplary embodiment, a distortion phenomenon of a reconstructed tomography image may be prevented. Thus, a tomography composition image having improved quality may be generated.

Exemplary embodiments may be implemented by computer programs in general-use computers that may execute the computer programs using a computer-readable recording medium. For example, the structure of data used in the above-described methods may be recorded in a computer-readable recording medium by using various methods. Examples of the computer-readable recording medium include magnetic storage media (e.g., ROM, RAM, USB, floppy disks, hard disks, etc.), and storage media such as optical recording media (e.g., CD-ROMs, or DVDs).

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art. Descriptions of features or aspects within each embodiment should typically be considered as available for other similar features or aspects in other embodiments.

What is claimed is:

1. A method of reconstructing a tomography image of an object from a plurality of projection images generated by scanning the object in a plurality of projection directions, the method comprising:
    determining whether a truncated portion of the object is present in each of the plurality of projection images;
    reconstructing a first reconstruction image by using at least one projection image, in which a truncated portion of the object is absent, based on a result of the determining;
    calculating projection data for the first reconstruction image, by using the first reconstruction image; and
    reconstructing a tomography image of the object by using the calculated projection data.

2. The method of claim 1, wherein the calculating the projection data comprises calculating the projection data corresponding to each of truncated projection images, in which the truncated portion of the object is present, based on a projection direction for each of the truncated projection images.

3. The method of claim 1, further comprising:
    estimating truncation data representing a truncated portion of the object with respect to at least one of truncated projection images, in which the truncated portion of the object is present, by using the calculated projection data,
    wherein the reconstructing the tomography image comprises reconstructing the tomography image of the object by using the estimated truncation data.

4. The method of claim 3, wherein the calculating the projection data comprises calculating the projection data corresponding to each of truncated projection images, in which the truncated portion of the object is present, based on a projection direction for each of the truncated projection images, and
    the estimating the truncation data comprises estimating the truncation data of each of the truncated projection images, by using the projection data corresponding to each of the truncated projection images.

5. The method of claim 4, wherein the projection data is calculated by being projected in the same projection direction as a corresponding truncated projection image.

6. The method of claim 3, further comprising correcting the estimated truncation data by using a sum of intensity values of the at least one projection image in which the truncated portion of the object is absent and a sum of intensity values of the truncated projection image corresponding to the estimated truncation data,
    wherein the reconstructing the tomography image comprises reconstructing the tomography image of the object by using the corrected truncation data.

7. The method of claim 6, wherein the correcting the estimated truncation data comprises correcting scaling errors in the estimated truncation data by subtracting the sum of the intensity values of the truncated projection image corresponding to the estimated truncation data from the sum of the intensity values of the at least one projection image in which the truncated portion is absent.

8. The method of claim 1, wherein the reconstructing the tomography image comprises reconstructing the tomography image by using the calculated projection data and at least one selected from a group consisting of the plurality of projection images, the at least one projection image in which the truncated portion of the object is absent, and the first reconstruction image.

9. The method of claim 1, wherein the calculating the projection data comprises calculating the projection data based on a projection operation for the first reconstruction image based on an assumption that a virtual detector detects a detection signal for a truncated portion of the object.

10. The method of claim 1, wherein the determining whether the truncated portion of the object is present comprises determining that the truncated portion of the object is present in the projection image, when the projection image includes a point after which data indicating a presence of the object is suddenly discontinued.

11. The method of claim 1, further comprising:
calculating an error between verification data which excludes truncation data, which corresponds to a truncated portion of the object, from projection data of images, on which the reconstructed tomography image has been projected in a plurality of projection directions, and the plurality of projection images generated by scanning the object in the plurality of projection directions;
verifying whether the calculated error satisfies a predetermined condition; and
updating the projection data for the tomography image by using the calculated error when the calculated error does not satisfy the predetermined condition.

12. The method of claim 11, wherein the reconstructing comprises reconstructing the tomography image of the object by using the updated projection data.

13. A non-transitory computer-readable recording medium having recorded thereon a program for executing the method of claim 1.

14. An apparatus for reconstructing a tomography image of an object from a plurality of projection images generated by scanning the object in a plurality of projection directions, the apparatus comprising:
a determinator that determines whether a truncated portion of the object is present in each of the plurality of projection images;
a first reconstructor that reconstructs a first reconstruction image by using at least one projection image, in which a truncated portion of the object is absent, based on a result of the determining;
a calculator that calculates projection data for the first reconstruction image, by using the first reconstruction image; and
a second reconstructor that reconstructs a tomography image of the object by using the calculated projection data.

15. The apparatus of claim 14, wherein the calculator calculates projection data corresponding to each of truncated projection images, in which the truncated portion of the object is present, based on a projection direction for each of the corresponding truncated projection images.

16. The apparatus of claim 14, further comprising:
an estimator that estimates truncation data representing a truncated portion of the object with respect to at least one of truncated projection images, in which the truncated portion of the object is present, by using the calculated projection data,
wherein the second reconstructor reconstructs the tomography image of the object by using the estimated truncation data.

17. The apparatus of claim 16, further comprising a corrector that corrects the estimated truncation data by using a sum of intensity values of the at least one projection image in which the truncated portion of the object is absent and a sum of intensity values of the truncated projection image,
wherein the second reconstructor reconstructs the tomography image of the object by using the corrected truncation data.

18. The apparatus of claim 14, further comprising:
a verifier that calculates an error between verification data which excludes truncation data, which corresponds to a truncated portion of the object, from projection data of images, on which the reconstructed tomography image has been projected in a plurality of projection directions, and the plurality of projection images generated by scanning the object in the plurality of projection directions, and verifies whether the calculated error satisfies a predetermined condition; and
an updater that updates the projection data for the tomography image by using the calculated error when the calculated error does not satisfy the predetermined condition.

19. A tomography apparatus comprising:
a radiation source that emits radiation toward an object in a plurality of projection directions;
a detector that detects a signal which is generated as the radiation emitted from the radiation source passes through the object and generates a plurality of projection images corresponding to the plurality of projection directions; and
an image reconstruction apparatus that reconstructs a first reconstruction image by using at least one projection image, in which a truncated portion of the object is absent, calculates projection data for the first reconstruction image, and reconstructs a tomography image of the object by using the calculated projection data.

20. The tomography apparatus of claim 19, wherein the image reconstruction apparatus estimates truncation data representing a truncated portion of the object with respect to a truncated projection image, in which the truncated portion of the object is present, by using the calculated projection data, and reconstructs the tomography image of the object by using the estimated truncation data.

* * * * *